(12) United States Patent
Li

(10) Patent No.: US 10,506,964 B2
(45) Date of Patent: Dec. 17, 2019

(54) DEVICE AND METHOD FOR DETECTING FATIGUE DRIVING

(71) Applicant: BOE Technology Group Co., Ltd., Beijing (CN)

(72) Inventor: Yingyi Li, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 16/023,439

(22) Filed: Jun. 29, 2018

(65) Prior Publication Data

US 2019/0046100 A1 Feb. 14, 2019

(30) Foreign Application Priority Data

Aug. 8, 2017 (CN) .......................... 2017 1 0670979

(51) Int. Cl.
*A61B 5/18* (2006.01)
*B60Q 9/00* (2006.01)
(Continued)

(52) U.S. Cl.
CPC .............. *A61B 5/18* (2013.01); *A61B 5/0006* (2013.01); *A61B 5/048* (2013.01); *A61B 5/0476* (2013.01); *A61B 5/225* (2013.01); *A61B 5/6803* (2013.01); *A61B 5/6893* (2013.01); *A61B 5/741* (2013.01); *A61B 5/746* (2013.01); *B60Q 9/00* (2013.01); *G08B 21/06* (2013.01);
(Continued)

(58) Field of Classification Search
CPC combination set(s) only.
See application file for complete search history.

(56) References Cited

U.S. PATENT DOCUMENTS

| 3,026,503 A * | 3/1962 | Scheer ................ B60K 28/06 180/272 |
| 2001/0028309 A1* | 10/2001 | Torch ................. A61B 3/0066 340/575 |
| 2015/0217687 A1 | 8/2015 | Colvin, Sr. |
| 2016/0068103 A1* | 3/2016 | McNew ................ B60Q 9/00 701/23 |

(Continued)

FOREIGN PATENT DOCUMENTS

| CN | 2048359 U | 11/1989 |
| CN | 205405810 U | 7/2016 |
| CN | 104802800 B | 8/2016 |
| CN | 106355837 A | 1/2017 |
| CN | 106394402 A | 2/2017 |
| CN | 106515644 A | 3/2017 |

(Continued)

OTHER PUBLICATIONS

Madhavi et al., "Understanding alcohol use disorders with neuroelectroscophysiology", 2014; National Institutes of Health Handbook of Clinical Neurology; 125:383-414. (Year: 2014).*

(Continued)

*Primary Examiner* — Nabil H Syed
*Assistant Examiner* — Cal J Eustaquio
(74) *Attorney, Agent, or Firm* — Nath, Goldberg & Meyer; Joshua B. Goldberg

(57) ABSTRACT

This disclosure provides a device and method for detecting fatigue driving. The device for detecting fatigue driving comprises: a first detection unit, which is disposed on a steering wheel of a vehicle, and configured to detect a grip of a driver on the steering wheel and transmit the detected grip value; and a controller, which is configured to receive the detected grip value, and determine whether the driver is in a suspected fatigue driving state according to the detected grip value and a grip standard sample value.

10 Claims, 2 Drawing Sheets

(51) Int. Cl.
*A61B 5/0476* (2006.01)
*A61B 5/00* (2006.01)
*A61B 5/22* (2006.01)
*A61B 5/048* (2006.01)
*G08B 21/06* (2006.01)
*A61B 5/04* (2006.01)
*B60W 40/08* (2012.01)

(52) U.S. Cl.
CPC ......... *A61B 5/04012* (2013.01); *A61B 5/7405* (2013.01); *A61B 5/7455* (2013.01); *A61B 2562/0247* (2013.01); *B60W 2040/0827* (2013.01)

(56) References Cited

U.S. PATENT DOCUMENTS

2017/0166054 A1* 6/2017 Ayala Rodriguez ........................ B60K 28/063

FOREIGN PATENT DOCUMENTS

| DE | 10 2009 050 763 A1 | 6/2010 |
|----|--------------------|--------|
| WO | 00/44580 A1 | 8/2000 |

OTHER PUBLICATIONS

Office Action dated Dec. 20, 2018 issued in corresponding Chinese Application No. 201710670979.7.

* cited by examiner

DEVICE AND METHOD FOR DETECTING FATIGUE DRIVING

CROSS-REFERENCE TO RELATED APPLICATION

This application claims the priority of Chinese Patent Application No. 201710670979.7 submitted to the Chinese Intellectual Property Office on Aug. 8, 2017, the disclosure of which is incorporated herein in its entirety by reference.

TECHNICAL FIELD

This disclosure relates to the technical field of automobile safety driving, and particularly relates to a device and method for detecting fatigue driving.

BACKGROUND

Among the causes of frequent traffic accidents, fatigue driving is one of the most important factors. After driving for a long period of time, the driver will have a disorder of physiological function and psychological function, followed by decline of the driving skill.

According to related statistics, if the driver's fatigue state can be detected and the driver can be promptly alerted when a fatigued driving is found, the reaction time of the driver can be shortened by 0.5 second, and the probability of traffic accidents can be reduced by 60%. Thus, in order to guarantee safety driving, there is a great significance in real-time monitoring and quantitative judgment of the driver's fatigue state during driving.

SUMMARY

The present disclosure has been accomplished in order to at least partially solve the problems in the existing art. The present disclosure provides a device and method for detecting fatigue driving that can reduce traffic accidents caused by fatigue driving.

According to one aspect of the disclosure, there is provided a device for detecting fatigue driving, comprising:

a first detection unit, which is disposed on a steering wheel of a vehicle, and configured to detect a grip of a driver on the steering wheel and transmit the detected grip value; and a controller, which is configured to receive the detected grip value, and determine whether the driver is in a suspected fatigue driving state according to the detected grip value and a grip standard sample value.

The first detection unit may be configured to detect the grip of the driver on the steering wheel based on a preset detection period;

the controller may be configured to calculate a mean value of the detected grip values during a current processing period, average the mean value and a grip standard sample value of a previous processing period to obtain a grip standard sample value of the current processing period; and determine whether the driver is in a suspected fatigue driving state according to the mean value of the detected grip values during the current processing period and the grip standard sample value of the current processing period; and the processing period is greater than the detection period.

The controller may be configured to calculate a difference between the detected grip value and the grip standard sample value, as well as an offset ratio indicating a ratio of the difference to the grip standard sample value; compare the offset ratio with a preset first threshold, and determine that the driver is in a suspected fatigue driving state when the offset ratio is greater than or equal to the first threshold.

The first detection unit may be disposed at an outer edge of the steering wheel;

when the vehicle is a left hand drive vehicle, the first detection unit is disposed at a left half edge or whole circumference of the steering wheel; and when the vehicle is right hand drive vehicle, the first detection unit is disposed at a right half edge or whole circumference of the steering wheel.

The device for detecting fatigue driving may further include a second detection unit head-wearable by the driver, and the second unit may include:

a detection member, which is configured to fit to a head of the driver and detect a brain wave amplitude of the driver; and a communication member, which is configured to transmit a detected value of the brain wave amplitude to the controller, and transmit a control instruct from the controller to the detection member, and the controller is configured to, when determining that the driver is in a suspected fatigue driving state, control to open the detection member via the communication member, and determine whether the driver is in a fatigue driving state according to the detected value of the brain wave amplitude and preset second and third thresholds.

The controller may be configured to calculate a difference between the second threshold and the detected value of the brain wave amplitude, as well as a fluctuation ratio indicating a ratio of the difference to the second threshold; compare the fluctuation ratio with the preset third threshold, and determine that the driver is in a fatigue driving state when the fluctuation ratio is smaller than or equal to the third threshold.

There may be a plurality of second thresholds and a plurality of third thresholds, and a corresponding relationship among a brain wave frequency range, the second threshold and the third threshold is prestored in the controller;

the detection member is further configured to detect a brain wave frequency of the driver, and transmit a detected value of the brain wave frequency to the controller; and the controller is further configured to, before calculating the difference between the second threshold and the detected value of the brain wave amplitude, determine the corresponding second and third thresholds according to the detected value of the brain wave frequency and the corresponding relationship.

There may be a plurality of detection members; and the controller is configured to calculate a fluctuation ratio corresponding to a detected value of the brain wave amplitude detected by each of the detection members, respectively, compare each of the fluctuation ratios with the corresponding third threshold, and determine that the driver is in a fatigue driving state when at least one of the fluctuation ratios is smaller than or equal to the third threshold.

The second detection member may be glasses, on a leg of which the detection member is disposed;

the second detection member further includes a power supply member, which is connected to the detection member and the communication member via a lead within a frame of the glasses; and the communication member is a wireless communication member.

The device for detecting fatigue driving further includes a warning unit, the warning unit is configured to warn the driver; and the controller is further configured to control to open the warning unit when determining that the driver is in a suspected fatigue driving state or fatigue driving state.

According to another aspect of the disclosure, there is provided a method for detecting fatigue driving, comprising:

by a first detection unit disposed on a steering wheel of a vehicle, detecting a grip of a driver on the steering wheel and transmitting the detected grip value; and by a controller, receiving the detected grip value, and determining whether the driver is in a suspected fatigue driving state according to the detected grip value and a grip standard sample value.

The method for detecting fatigue driving may further include:

by a detection member fitting to a head of the driver, detecting a brain wave amplitude of the driver; and by the controller, determining whether the driver is in a fatigue driving state according to the detected value of the brain wave amplitude and preset second and third thresholds.

The controller controls to open the detection member when determining that the driver is in a suspected fatigue driving state.

The method for detecting fatigue driving may further include:

by a warning unit, warning the driver.

DETAILED DESCRIPTION

The exemplary embodiments of the disclosure will now be described clearly and completely in conjunction with the accompanying drawings. Obviously, the described exemplary embodiments are part, but not all, of the embodiments of the disclosure. Based on the exemplary embodiments of the disclosure, all the other embodiments obtained by those skilled in the art without any creative labor fall into the protection scope of the disclosure.

Figure 1:
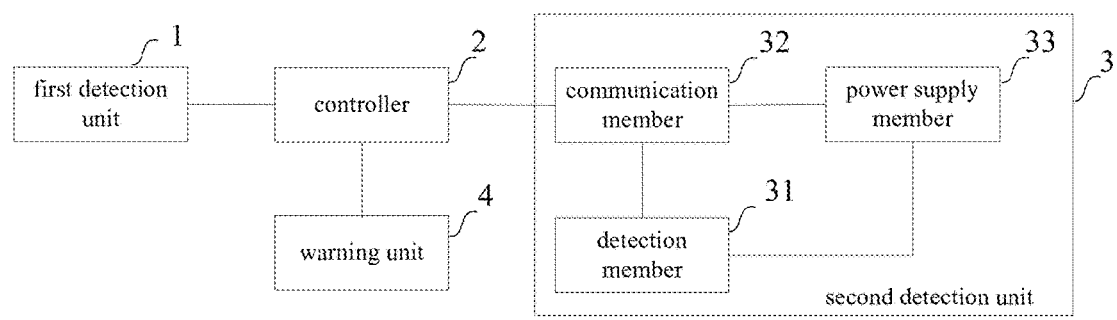
FIG. 1 is a schematic view showing a configuration of a device for detecting fatigue driving according to an exemplary embodiment of the disclosure.

According to one aspect of the disclosure, this disclosure provides a device for detecting fatigue driving. As shown in FIG. 1, the device for detecting fatigue driving includes a first detection unit 1 and a controller 2. The first detection unit 1 is disposed on a steering wheel of a vehicle, and configured to detect a grip of a driver on the steering wheel and transmit the detected grip value to the controller 2. The controller 2 is configured to determine whether the driver is in a suspected fatigue driving state according to the detected grip value and a grip standard sample value.

In an exemplary embodiment of the disclosure, the first detection unit 1 may be a pressure sensor. However, the first detection unit 1 of the disclosure is not limited thereto, but may be any other unit or circuit capable of detecting a force. In an exemplary embodiment of the disclosure, the controller 2 may be an Electronic Control Unit (ECU) on a vehicle. However, the controller 2 of the disclosure is not limited thereto, but may be implemented by a DSP chip or embedded chip.

It should be noted that the grip standard sample value may be a fixed value preset in the controller 2, or the grip standard sample value may be a reference value learned by the controller 2 through continuous trainings.

The device for detecting fatigue driving provided in the disclosure includes the controller 2, and the first detection unit 1 on the steering wheel of the vehicle for detecting a grip of the driver on the steering wheel. Generally, when fatigue driving occurs, the grip of the driver on the steering wheel will change greatly. Thus, according to the detected grip value and the grip standard sample value, the controller 2 may determine whether the driver is in a suspected fatigue driving state, thereby conducting a preliminary screening of the fatigue driving state timely, preparing in advance and effectively reducing or avoiding traffic accidents.

The first detection unit 1 has a preset detection period, according to which the first detection unit 1 detects the grip of the driver on the steering wheel. The controller 2 has a preset processing period which is greater than the detection period. That is, the time of the controller 2 spent in one processing period is longer than the time of the first detection unit 1 spent in one detection period.

In one exemplary embodiment of the disclosure, the controller 2 is specifically configured to calculate a mean value of the detected grip values during a current processing period, and average the mean value and a grip standard sample value of a previous processing period to obtain a grip standard sample value of the current processing period; and determine whether the driver is in a suspected fatigue driving state according to the mean value of the detected grip values during the current processing period and the grip standard sample value of the current processing period.

That is, the controller 2 obtains a grip standard sample value of the current driver through sample trainings on the detected grip values detected by the first detection unit 1. Specifically, when a processing period during which the first detection unit 1 detects a plurality of detected grip values is ended, the controller 2 calculates a mean value of the detected grip values during the processing period, and averages the mean value of the detected grip values during the processing period and the grip standard sample value of a previous processing period to obtain a grip standard sample value of the processing period. When the grip standard sample value of the current processing period is determined, it can be used to determine a current grip of the driver, thereby determining whether the driver is in a suspected fatigue driving state.

In an exemplary embodiment of the disclosure, the controller 2 has a preset first threshold therein, which is a ratio, such as 15-20%.

The controller 2 may be specifically configured to calculate a difference between the detected grip value and the grip standard sample value, as well as an offset ratio indicating a ratio of the difference to the grip standard sample value; compare the offset ratio with a preset first threshold, and determine that the driver is in a suspected fatigue driving state when the offset ratio is greater than or equal to the first threshold.

It should be noted that in an exemplary embodiment of the disclosure, the difference between the detected grip value and the grip standard sample value is an absolute value, i.e., the determining result will not be affected whether the detected grip value is greater or smaller than the grip standard sample value. In the calculation of the difference between the detected grip value and the grip standard sample value, the detected grip value is a mean value of detected grip values during the processing period, the grip standard sample value is a grip standard sample value of the current processing period calculated from the grip standard sample value of the previous processing period and the detected grip values during the current processing period, and in the calculation of the offset ratio, the denominator is also the grip standard sample value of the current processing period. Thus, by calculating the offset ratio using the grip standard sample value of the current processing period, and by reflecting the offset degree of the detected grip value using the offset ratio, the determining result of the fatigue state will be more precise and reasonable.

A position of the first detection unit 1 will now be described in detail with reference to FIGS. 2a and 2b.

Generally, during driving, the palm rests on an outer edge of a steering wheel 5, four fingers naturally hold an inner side of the steering wheel 5, and the thumb attaches to an inner edge of the steering wheel 5. Thus, as shown in FIGS. 2a and 2b, the first detection unit 1 may be disposed at the outer edge of the steering wheel 5. As a result, the detection result will be more precise since the contact area between the palm and the steering wheel is the largest.

Figure 2A:
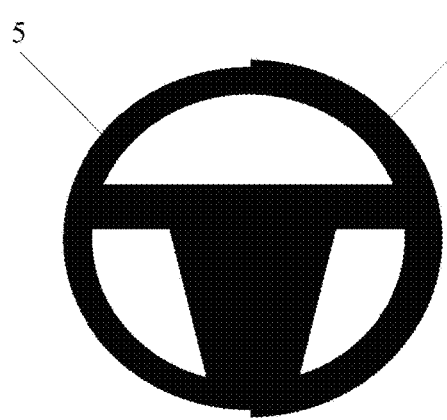
FIG. 2a is a schematic view showing a first detection unit mounted on a steering wheel of a right hand drive vehicle according to an exemplary embodiment of the disclosure.

As shown in FIG. 2a, when the vehicle is a right hand drive vehicle, the first detection unit 1 may be disposed at a right half edge or whole circumference of the steering wheel 5. For a right hand drive vehicle, if the vehicle has a manual transmission, the grip measurement data will have a greater error at the left half edge of the steering wheel 5 (i.e., from 6 o'clock to 12 o'clock) since a left hand of the driver needs to control gears. Therefore, the first detection unit 1 may be disposed at the right half edge of the steering wheel 5 (i.e., from 1 o'clock to 6 o'clock).

Figure 2B:
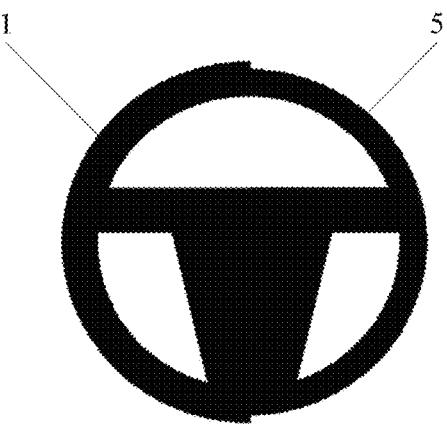
FIG. 2b is a schematic view showing a first detection unit mounted on a steering wheel of a left hand drive vehicle according to an exemplary embodiment of the disclosure.

As shown in FIG. 2b, when the vehicle is a left hand drive vehicle, the first detection unit 1 is disposed at a left half edge or whole circumference of the steering wheel 5. For a left hand drive vehicle, if the vehicle has a manual transmission, the grip measurement data will have a greater error at the right half edge of the steering wheel 5 (i.e., from 1 o'clock to 6 o'clock) since a right hand of the driver needs to control gears. Therefore, the first detection unit 1 may be disposed at the left half edge of the steering wheel 5 (i.e., from 6 o'clock to 12 o'clock).

It should be noted that for a vehicle with an automatic transmission, the first detection unit 1 may be disposed on the whole (i.e., a range of 360°) outer edge of the steering wheel 5 since there is no need for manual shift.

Figure 3:
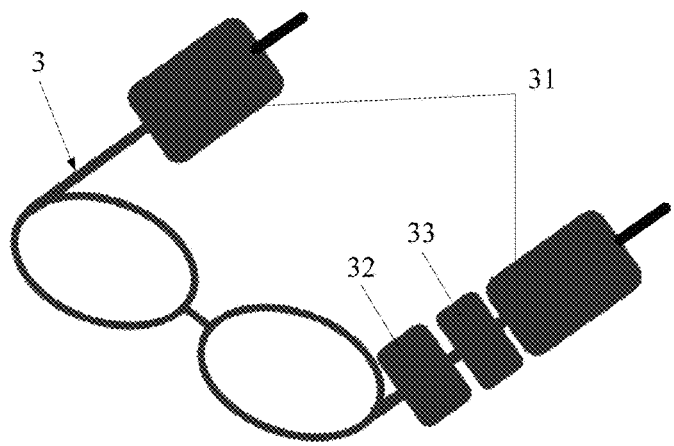
FIG. 3 is a structural schematic view showing a second detection unit according to an exemplary embodiment of the disclosure.

In order to further improve precision in detection of the fatigue state of the driver, as shown in FIGS. 1 and 3, the device for detecting fatigue driving may further include a second detection unit 3 configured to be head-wearable by a driver. The second detection unit 3 may be a hat, helmet, scarf, glasses or the like. In an exemplary embodiment of the disclosure, it will take the second detection unit being glasses as an example for detailed explanation.

An unexpected event during driving may also cause the driver's grip on the steering wheel to change, such as the hand leaving the steering wheel to pick up something. Therefore, determination purely based on the grip of the driver on the steering wheel can only be used as a preliminary determination of a fatigued driving state. Therefore, in an exemplary embodiment of the disclosure, when it is determined that the driver is in a suspected fatigue driving state, the brain wave of the driver is further detected to finally determine whether the driver is actually in a fatigue driving state.

As shown in FIGS. 1 and 3, the second detection unit 3 includes a detection member 31 and a communication member 32. The detection member 31 fits to the head of the driver, and is configured to detect a brain wave amplitude of the driver. The communication member 32 is configured to transmit a detected value of the brain wave amplitude to the controller 2, and transmit a control instruct from the controller 2 to the detection member 31.

The controller 2 is further configured to, when determining that the driver is in a suspected fatigue driving state, control to open the detection member 31 via the communication member 32, and determine whether the driver is in a fatigue driving state according to the detected value of the brain wave amplitude and preset second and third thresholds. The controller 2 has therein the preset second threshold corresponding to a brain wave amplitude, different types of brain waves corresponding to different second thresholds, and the preset third threshold being a ratio, such as 15-20%.

In an exemplary embodiment of the disclosure, the controller 2 is specifically configured to calculate a difference between the second threshold and the detected value of the brain wave amplitude, as well as a fluctuation ratio indicating a ratio of the difference to the second threshold; compare the fluctuation ratio with the preset third threshold, and determine that the driver is in a fatigue driving state when the fluctuation ratio is smaller than or equal to the third threshold.

It should be noted that generally, when a person is in a fatigue state, brain activities are reduced and brain waves are inactive. Accordingly, the brain wave amplitude decreases. Therefore, in the exemplary embodiment of the disclosure, the difference between the second threshold and the detected value of the brain wave amplitude is obtained by subtracting the detected value of the brain wave amplitude from the second threshold.

By monitoring the grip of the driver on the steering wheel, this disclosure makes a preliminary determination on whether the driver is in a fatigue driving state, and when determining that the driver is in a suspected fatigue driving state, the disclosure further detects the brain wave activity of the driver, so as to determine whether the driver is actually in a fatigue driving state. Such detection is timely, effective, and accurate, thus can effectively reduce or avoid traffic accidents.

Brain waves are spontaneous, rhythmic neural electrical activity with a frequency range from 1 to 30 times per second, which can be divided into four bands: $\delta$-wave (1-3 Hz), $\theta$-wave (4-7 Hz), a wave (8-13 Hz), and $\beta$ wave (14-30 Hz).

In an exemplary embodiment of the disclosure, one detection member 31 may be used to detect several types of brain waves. In this case, there may be a plurality of second thresholds and a plurality of third thresholds, and a corresponding relationship among the brain wave frequency range and the second and third thresholds is prestored in the controller 2.

The detection member 31 is further configured to detect a brain wave frequency of the driver, and transmit a detected value of the brain wave frequency to the controller 2. The controller 2 is further configured to, before calculating the difference between the second threshold and the detected value of the brain wave amplitude, determine the corresponding second and third thresholds according to the detected value of the brain wave frequency and the corresponding relationship.

Each brain wave frequency range corresponds to a respective type of brain waves, and the controller 2 determines a frequency range of the detected brain waves according to a magnitude of the detected brain wave frequency, and then according to the corresponding relationship among the brain wave frequency range and the second and third thresholds, determines the corresponding second and third thresholds, and then calculates the fluctuation ratio according to the determined second threshold, and determines whether the driver is actually in a fatigue driving state according to the determined third threshold.

In order to further improve precision in determination of the fatigue driving state, in an exemplary embodiment of the disclosure, there may be a plurality of detection member 31 to detect various types of brain waves, respectively. Accordingly, the controller 2 determines the fatigue driving regarding different types of brain waves, and obtains a final determination by integrating the determinations on fatigue driving states of various types of brain waves.

Specifically, the controller 2 is configured to calculate a fluctuation ratio corresponding to a detected value of the brain wave amplitude detected by each of the detection members 31, respectively, compare each of the fluctuation ratios with the corresponding third threshold, and determine that the driver is in a fatigue driving state when at least one of the fluctuation ratios is smaller than or equal to the corresponding third threshold.

That is, the driver is not considered to be in a fatigue driving state currently only when all the detect brain waves are active. In this way, interference situations can be effectively eliminated, making the device for detecting fatigue driving more reliable.

As shown in FIGS. 1 and 3, in an exemplary embodiment of the disclosure, the second detection unit 3 is glasses, on a leg of which the detection member 31 is disposed. The data detection is more accurate since the leg of the glasses is closer to the cortex. In the exemplary embodiment of the disclosure, there are two detection members 31 disposed on respective legs of the glasses. The second detection unit 3 further includes a power supply member 33. In an exemplary embodiment of the disclosure, there is one power supply member 33 and one communication member 32. The power supply member 33 is connected to the detection member 31 and the communication member 32 via a lead, and configured to supply power for the detection member 31 and the communication member 32. The lead is inside of a frame of the glasses, i.e., the frame has a hollow structure within which the lead is received and prevented from being exposed. In this way, it is more convenient to wear.

In an exemplary embodiment of the disclosure, the detection member 31 may be a sensor, such as a brain wave sensor, or may be implemented by a DSP chip or embedded chip. However, the detection member 31 of the disclosure is not limited thereto, but may be any other unit or detection circuit capable of detecting brain waves. In an exemplary embodiment of the disclosure, the power supply member 33 may be a cell, such as a minicell. However, the power supply member 33 of the disclosure is not limited thereto, but may be any other unit or power supply circuit capable of supplying power. In addition, in an exemplary embodiment of the disclosure, the communication member 32 may be a wireless communication member, for example, Bluetooth, ZigBee, Wifi (Wireless Fidelity) or other communication members. However, the communication member 32 of the disclosure is not limited thereto, but may be any other device or communication circuit capable of communication.

In an exemplary embodiment of the disclosure, as shown in FIG. 1, the device for detecting fatigue driving may further include a warning unit 4, which is configured to warn the driver. The controller 2 is further configured to control to open the warning unit 4 when determining that the driver is in a suspected fatigue driving state or fatigue driving state.

In an exemplary embodiment of the disclosure, the warning unit 4 may be an electrostatic discharge unit, which may be disposed on the steering wheel 5, the second detection unit 3 or a vehicle seat, and configured to stimulate the driver to increase his/her attention. However, the warning unit 4 of the disclosure is not limited thereto, but may be any other unit (e.g., a voice announcer) or warning circuit capable of stimulating the driver.

Figure 4:
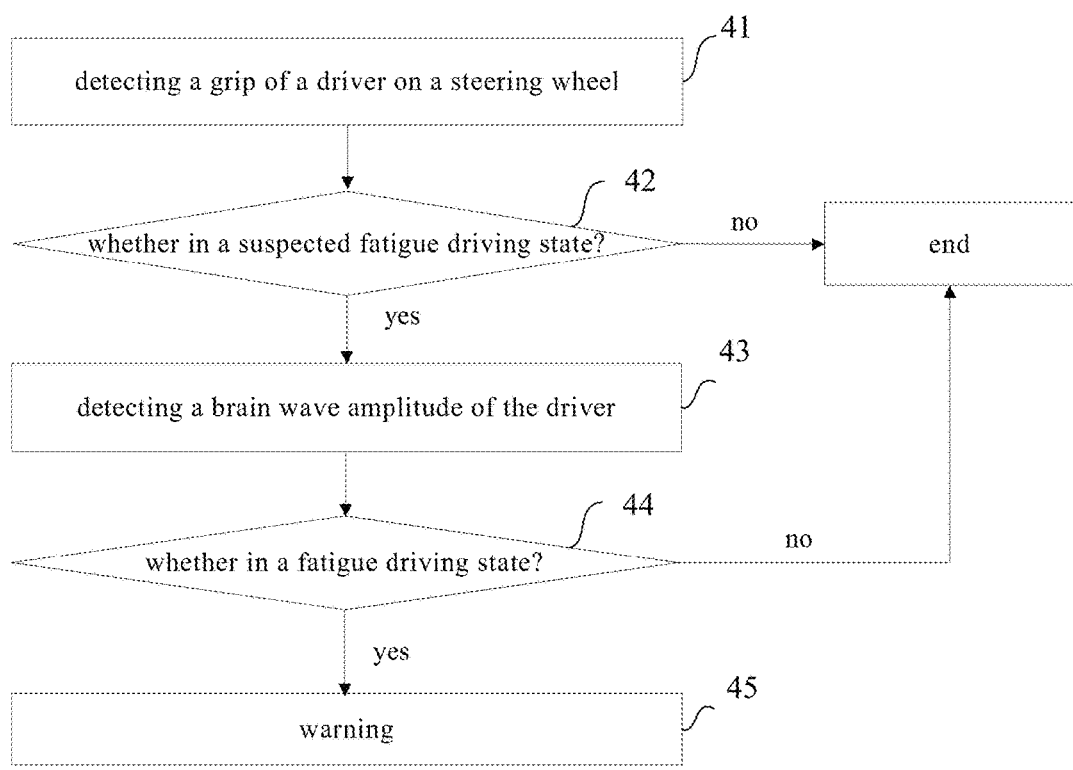
FIG. 4 is a flowchart of the method for detecting fatigue driving according to an exemplary embodiment of the disclosure.

According to another aspect of the disclosure, this disclosure provides a method for detecting fatigue driving. In order to clearly illustrate the exemplary embodiment of the disclosure, the method for detecting fatigue driving will now be described in detail with reference to FIGS. 1, 3 and 4. The method for detecting fatigue driving of the disclosure is based on the above discussed device for detecting fatigue driving of the disclosure. As shown in FIG. 4, the method includes steps 41-45.

At step 41, detecting a grip of a driver on the steering wheel.

In an exemplary embodiment of the disclosure, a first detection unit 1 disposed on the steering wheel of the vehicle detects the grip of the driver on the steering wheel based on a preset detection period and transmits the detected grip value to the controller 2.

At step 42, by the controller 2, determining whether the driver is in a suspected fatigue driving state according to the detected grip value and a grip standard sample value. If so, move to Step 43; otherwise, the procedure is ended.

In an exemplary embodiment of the disclosure, the controller 2 calculates a mean value of the detected grip values during a current processing period, averages the mean value and a grip standard sample value of a previous processing period to obtain a grip standard sample value of the current processing period, and determines whether the driver is in a suspected fatigue driving state according to the mean value of the detected grip values during the current processing period and the grip standard sample value of the current processing period.

The controller 2 may calculate a difference between the detected grip value and the grip standard sample value, as well as an offset ratio, compare the offset ratio with a preset first threshold, and determine that the driver is in a suspected fatigue driving state when the offset ratio is greater than or equal to the first threshold. If so, move to Step 43; otherwise, it is determined that the driver is in a normal driving state, and the procedure is ended.

At step 43, detecting a brain wave amplitude of the driver.

In an exemplary embodiment of the disclosure, the second detection unit 3 is worn on and fits to the head of the driver. When determining that the driver is in a suspected fatigue driving state, the controller 2 controls to open the detection member 31 via the communication member 32 so that the detection member 31 detects a brain wave amplitude of the driver and the communication member 32 transmits a detected value of the brain wave amplitude to the controller 2.

At step 44, by the controller 2, determining whether the driver is in a fatigue driving state according to the detected value of the brain wave amplitude and preset second and third thresholds. If so, move to Step 45; otherwise, the procedure is ended.

In an exemplary embodiment of the disclosure, the controller 2 determines whether the driver is in a fatigue driving state according to the detected value of the brain wave amplitude and the preset second and third thresholds. In that, the controller 2 calculates a difference between the second threshold and the detected value of the brain wave amplitude, as well as a fluctuation ratio, compares the fluctuation ratio with the third threshold, and determines that the driver is in a fatigue driving state when the fluctuation ratio is smaller than or equal to the third threshold. If so, move to Step 45; otherwise, it is determined that the driver is in a normal driving state, and the procedure is ended.

At step 45, warning.

In an exemplary embodiment of the disclosure, when determining that the driver is in a fatigue driving state, the controller 2 controls to open the warning unit 4 to remind the driver to increase his/her attention.

It should be noted that in Step 42, when the controller 2 determines that the driver is in a suspected fatigue driving state, it may also move to Step 45 to make warning.

By providing a first detection unit 1 on the steering wheel 5 to detect a grip of the driver, the device for detecting fatigue driving of the disclosure may determine a driving state without interfering with the driver. The method for determining a fatigue state according to information about the grip of the driver on the steering wheel of the disclosure can automatically learn and train the grip standard sample value, thereby obtaining a more precise determination result. By shaping the second detection unit 3 into glasses and using a plurality of detection members 31, multi-point detection is realized and the data is more accurate. By using the communication member 32 as a wireless communication member, the brain wave data signal may be transmitted to the controller 2 wirelessly without any physical connection with data cables. By detecting the brain waves with the second detection unit 3, the driver's accurate biological signal under the fatigue driving state can be reflected, thereby accurately reflecting the driver's fatigue degree. By using the detected grip value as input information and the detected value of the brain wave amplitude as auxiliary input information, and by quantifying fatigue result and using quantified data as output information, the disclosure established a complete device for detecting fatigue driving safety.

The controller 2 of the disclosure carries out autonomous training through, for example, grip sample collection, judgment standard construction, and device training parameter learning, establishes a highly targeted fatigue driving judgment standard for different driving habits of different drivers (i.e., the grip standard sample value), and automatically trains and updates the grip standard sample value after a certain period of time so that the precision in judgment can be continuously improved.

It should be understood that the above embodiments are merely exemplary embodiments for the purpose of illustrating the principle of the disclosure, and the disclosure is not limited thereto. Various modifications and improvements can be made by a person having ordinary skill in the art without departing from the spirit and essence of the disclosure. Accordingly, all of the modifications and improvements also fall into the protection scope of the disclosure

What is claimed is:

1. A device for detecting fatigue driving, comprising:
   a first detection apparatus, which is disposed on a steering wheel of a vehicle, and configured to detect a grip of a driver on the steering wheel and transmit the detected grip value;
   a controller, which is configured to receive the detected grip value, and determine whether the driver is in a suspected fatigue driving state according to the detected grip value and a grip standard sample value; and
   a second detection apparatus head-wearable by the driver, wherein the second detection apparatus comprises:
      a detection member, which is configured to fit to a head of the driver and detect a brain wave amplitude of the driver; and
      a communication member, which is configured to transmit a detected value of the brain wave amplitude to the controller, and transmit a control instruct from the controller to the detection member,
   wherein the controller is configured to, when determining that the driver is in a suspected fatigue driving state, control to activate the detection member via the communication member, and determine whether the driver is in a fatigue driving state according to the detected value of the brain wave amplitude and preset second and third thresholds, and
   wherein the controller is configured to calculate a difference between the second threshold and the detected value of the brain wave amplitude, as well as a fluctuation ratio indicating a ratio of the difference to the second threshold; compare the fluctuation ratio with the preset third threshold, and determine that the driver is in a fatigue driving state when the fluctuation ratio is smaller than or equal to the third threshold.

2. The device for detecting fatigue driving of claim 1, wherein
   the first detection apparatus is configured to detect the grip of the driver on the steering wheel based on a preset detection period;
   the controller is configured to calculate a mean value of the detected grip values during a current processing period, average the mean value and a grip standard sample value of a previous processing period to obtain a grip standard sample value of the current processing period; and determine whether the driver is in a suspected fatigue driving state according to the mean value of the detected grip values during the current processing period and the grip standard sample value of the current processing period; and
   the processing period is greater than the detection period.

3. The device for detecting fatigue driving of claim 2, wherein
   the controller is configured to calculate a difference between the detected grip value and the grip standard sample value, as well as an offset ratio indicating a ratio of the difference to the grip standard sample value; compare the offset ratio with a preset first threshold, and determine that the driver is in a suspected fatigue driving state when the offset ratio is greater than or equal to the first threshold.

4. The device for detecting fatigue driving of claim 1, wherein
   the first detection apparatus is disposed at an outer edge of the steering wheel;

when the vehicle is a left hand drive vehicle, the first detection apparatus is disposed at a left half edge or whole circumference of the steering wheel; and when the vehicle is right hand drive vehicle, the first detection apparatus is disposed at a right half edge or whole circumference of the steering wheel.

5. The device for detecting fatigue driving of claim 1, wherein there are a plurality of second thresholds and a plurality of third thresholds, and a corresponding relationship among a brain wave frequency range, the second threshold and the third threshold is prestored in the controller;

the detection member is further configured to detect a brain wave frequency of the driver, and transmit a detected value of the brain wave frequency to the controller; and the controller is further configured to, before calculating the difference between the second threshold and the detected value of the brain wave amplitude, determine the corresponding second and third thresholds according to the detected value of the brain wave frequency and the corresponding relationship.

6. The device for detecting fatigue driving of claim 1, wherein there are a plurality of detection members; and the controller is configured to calculate a fluctuation ratio corresponding to a detected value of the brain wave amplitude detected by each of the detection members, respectively, compare each of the fluctuation ratios with the corresponding third threshold, and determine that the driver is in a fatigue driving state when at least one of the fluctuation ratios is smaller than or equal to the third threshold.

7. The device for detecting fatigue driving of claim 1, wherein the second detection apparatus is glasses, on a leg of which the detection member is disposed;

the second detection apparatus further includes a power supply member, which is connected to the detection member and the communication member via a lead within a frame of the glasses; and the communication member is a wireless communication member.

8. The device for detecting fatigue driving of claim 1, further comprising a warning apparatus, wherein the warning apparatus is configured to warn the driver; and the controller is further configured to control to activate the warning apparatus when determining that the driver is in a suspected fatigue driving state or fatigue driving state.

9. A method for detecting fatigue driving, comprising:

by a first detection apparatus disposed on a steering wheel of a vehicle, detecting a grip of a driver on the steering wheel and transmitting the detected grip value;

by a controller, receiving the detected grip value, and determining whether the driver is in a suspected fatigue driving state according to the detected grip value and a grip standard sample value;

activating a detection member fitting to a head of the driver when the controller determines that the driver is in the suspected fatigue driving state;

by the detection member, detecting a brain wave amplitude of the driver; and by the controller, determining whether the driver is in a fatigue driving state according to the detected value of the brain wave amplitude and preset second and third thresholds, wherein the controller is configured to calculate a difference between the second threshold and the detected value of the brain wave amplitude, as well as a fluctuation ratio indicating a ratio of the difference to the second threshold; compare the fluctuation ratio with the preset third threshold, and determine that the driver is in a fatigue driving state when the fluctuation ratio is smaller than or equal to the third threshold.

10. The method for detecting fatigue driving of claim 9, further comprising:

by a warning apparatus, warning the driver.

* * * * *